US009717820B2

(12) United States Patent
Wang et al.

(10) Patent No.: US 9,717,820 B2
(45) Date of Patent: Aug. 1, 2017

(54) PROCOAGULANT PEPTIDES AND THEIR DERIVATIVES AND USES THEREFOR

(71) Applicant: Ethicon, Inc., Somerville, NJ (US)

(72) Inventors: Yi-Lan Wang, Somerset, NJ (US); Guanghui Zhang, Belle Mead, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 14/836,014

(22) Filed: Aug. 26, 2015

(65) Prior Publication Data
US 2015/0359925 A1    Dec. 17, 2015

Related U.S. Application Data

(62) Division of application No. 13/173,013, filed on Jun. 30, 2011, now Pat. No. 9,149,511.

(51) Int. Cl.
| | | |
|---|---|---|
| A61K 38/08 | (2006.01) | |
| A61K 38/17 | (2006.01) | |
| A61K 38/38 | (2006.01) | |
| A61P 17/02 | (2006.01) | |
| A61K 38/39 | (2006.01) | |
| A61L 24/00 | (2006.01) | |
| A61L 24/10 | (2006.01) | |
| A61L 26/00 | (2006.01) | |

(52) U.S. Cl.
CPC .......... *A61L 26/0052* (2013.01); *A61K 38/39* (2013.01); *A61L 24/0015* (2013.01); *A61L 24/108* (2013.01); *A61L 26/009* (2013.01); *A61L 2300/25* (2013.01); *A61L 2300/252* (2013.01); *A61L 2300/418* (2013.01); *A61L 2400/04* (2013.01)

(58) Field of Classification Search
CPC ................ A61K 2300/00; A61K 38/00; A61K 47/48238; A61K 38/57; A61K 51/1027; A61K 38/39; A61K 38/196; A61K 49/14; A61K 38/36; C07K 14/78; C07K 2319/70; G01N 33/86; G01N 2800/224; G01N 2333/75; G01N 2800/22; G01N 2800/222; G01N 2800/226; C12N 5/0691
See application file for complete search history.

(56) References Cited

U.S. PATENT DOCUMENTS

| 5,190,920 | A | 3/1993 | Eyal et al. | |
|---|---|---|---|---|
| 5,399,667 | A | 3/1995 | Frazier et al. | |
| 6,045,570 | A | 4/2000 | Epstein et al. | |
| 7,285,580 | B2 | 10/2007 | Stedronsky | |
| 2009/0068246 | A1* | 3/2009 | Kinney | A61K 38/39 424/423 |
| 2011/0045047 | A1 | 2/2011 | Bennett et al. | |
| 2011/0206771 | A1 | 8/2011 | Choi et al. | |
| 2013/0004478 | A1 | 1/2013 | Wang et al. | |

FOREIGN PATENT DOCUMENTS

| JP | 2011-513251 | 4/2011 | |
|---|---|---|---|
| WO | WO 96/40033 | 12/1996 | |
| WO | WO03/007845 | * 1/2003 | ............ A61K 38/39 |
| WO | WO 2007/044026 | 4/2007 | |
| WO | WO 2009/040034 | 4/2009 | |
| WO | WO 2009/153748 | 12/2009 | |
| WO | WO 2010/050787 | 5/2010 | |

OTHER PUBLICATIONS

Bonnefoy, A. et al.,"A Model of Platelet Aggregation Involving Multiple Interactions of Thrombospondin-1, Fibrinogen, and GPIIbIIIa Receptor" J. Biol. Chem. (2001) vol. 276, No. 8 pp. 5605-5612.
Bonnefoy, A. et al."The evolving role of thrombospondin-1(TSP1) in hemostasis and vascular biology" Cell. Mol. Life Sci. (2008) vol. 65 pp. 713-727.
Chung, J. et al. "Thrombspondin Acts via Integrin-associated Protein to Activate the Platelet Integrin αIIbb3" J. Biol. Chem. (1997) vol. 272, No. 23, Issue of Jun. 6, pp. 14740-14746.
Chung, J. et al."Thrombospondin-1 Acts Via IAP/CD47 to Synergize with Collagen in α2β1-Mediated Platelet Activation" Blood. (1999) vol. 94, Issue 2 pp. 642-648.
Dorahy, D.J. et al.,"Stimulation of Platelet Activation and Aggregation by a Carboxyl-terminal Peptide from Thrombospondin Binding to the Integrin-associated Protein Receptor" J. Biol Chem (1997) vol. 272 pp. 1323-1330.
Fujimoto, T-T et al."Thrombospondin-bound Integrin-associated Protein (CD47) Physically and Functionally Modifies Integrin αIIbβ3 by Its Extracellular Domain" J Biol Chem (2003) vol. 278, No. 29 pp. 26655-26665.
Trumel, C. et al., "Platelet aggregation induced by the C-terminal peptide of thrombospondin-1 requires the docking protein LAT but is largely independent of αIIb/β3" Journal of Thrombosis and Haemostasis (2003) vol. 1 pp. 320-329.
Tulasne, D. et al."C-terminal peptide of thrombospondin-1 induces platelet aggregation through the Fc receptor γ-chain-associated signaling pathway and by agglutination" Blood (2001) vol. 98, No. 12 pp. 3346-3352.
Tuszynski, G.P. et al"Thrombospondin Promotes Platelet Aggregation" Blood (1988) vol. 72, No. 1 pp. 109-115.

(Continued)

*Primary Examiner* — Satyanarayana R Gudibande
*Assistant Examiner* — Jia-Hai Lee
(74) *Attorney, Agent, or Firm* — David R. Crichton; Leo Kriksunov

(57) ABSTRACT

The present invention is directed to a hemostatic or tissue sealing material having (a) a peptide having a sequence SEQ ID NO: 1 or an amino acid analog sequence thereof, and (b) a scaffold for said peptide or amino acid analogue sequence. The scaffold is preferably hemostatic, such as a natural or genetically engineered absorbable polymer, a synthetic absorbable polymer, or combinations thereof. The natural or genetically engineered absorbable polymers can be selected from the group consisting of a protein, a polysaccharide, or combinations thereof.

15 Claims, 8 Drawing Sheets

(56) References Cited

OTHER PUBLICATIONS

Voit, S. et al. "The C-terminal peptide of thrombospondin-1 stimulates distinct signaling pathways but induces an activation-independent agglutination of platelets and other cells" FEBS Letters (2003) vol. 544 pp. 240-245.
Evithrom. Approval Letter by FDA (2007), 8 pages.
Jackson, S.P. 'The growing complexity of platelet aggregation' Blood (2007) Jun. 109(12) pp. 5087-5095.
Lew et al 'Clinical use of topical thrombin as a surgical hemostat' Biologics 2008 2(4) pp. 593-599.
Li et al 'Synthesis of Polyethylene Glycol (PEG) Derivatives and PEGylated-Peptide Biopolymer Conjugates' Biomacromolecules (2003) 4 pp. 1055-1067.
Otani, Y. et al 'Hemostatic capability of rapidly curable glues from gelatin poly(L-glutamic acide), and carbodiimide' Biomaterials 19 (1998) pp. 2091-2098.
Spotnitz, W.D. et al 'Hemostats, sealants and adhesives: components of the surgical toolbox' Transfusion vol. 48 (2008) pp. 1502-1516.
Surgiflo Hemostatic Matrix Product Instruction. Ethicon, Inc. (2012) 2 pages.
International Preliminary Report on Patentability re: PCT/US2012/042346 dated Sep. 5, 2013.
International Search Report re: PCT/US2012/042346 dated Feb. 25, 2013.

\* cited by examiner

PROCOAGULANT PEPTIDES AND THEIR DERIVATIVES AND USES THEREFOR

SEQUENCE LISTING

The instant application contains a Sequence Listing which has been submitted in ASCII format via EFS-Web and is hereby incorporated by reference in its entirety. Said ASCII copy, created on Jun. 28, 2011, is named ETH5623.txt and is 4,912 bytes in size.

FIELD OF THE INVENTION

The present invention relates generally to agents and devices for promoting hemostasis and tissue sealing materials and, more particularly, to synthetic peptides having strong hemostatic properties and tissue sealing properties in combination with scaffolds, such as gelatin based hemostatic scaffolds.

BACKGROUND

Blood is a liquid tissue that includes red cells, white cells, corpuscles, and platelets dispersed in a liquid phase. The liquid phase is plasma, which includes acids, lipids, dissolved electrolytes, and proteins. One particular protein suspended in the liquid phase is fibrinogen. When bleeding occurs, the fibrinogen reacts with water and thrombin (an enzyme) to form fibrin, which is insoluble in blood and polymerizes to form clots.

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances substantial bleeding can occur. These situations usually require specialized equipment and materials as well as personnel trained to administer appropriate aid.

In an effort to address the above-described problems, materials have been developed for controlling excessive bleeding.

The previously known materials, such as gelatin, collagen, oxidized cellulose, thrombin, fibrinogen, and other materials have been used, but each of these materials has limitations. For example, one type of prior art blood clotting materials are blood-derived proteins or enzymes, including fibrinogen and/or thrombin, which are expensive, need specialized storage conditions, and require extensive purification in order to eliminate the potential for transmission of blood-borne infections.

Hemostatic devices containing liquid thrombin have special handling requirements in order to maintain thrombin's biologic activity. For example, liquid thrombin requires refrigeration to maintain shelf-life stability. Safety is also a concern when using animal or human derived thrombin as there are some risks of contaminants or immunogenicity. Further, thrombin and fibrinogen purified from human or animal plasma are very expensive. Therefore, it is advantageous to develop novel hemostats with greater shelf-life stability, lower risk of viral etc. contaminants and lower immunogenicity, low cost, and which can work in heparinized blood.

Human protein Thrombospondin-1 (TSP-1) and related peptides were described in literature as to be involved in angiogenesis and platelet aggregation. TSP-1 is a homotrimeric glycoprotein (MW ~450K) and was first discovered in platelets as a thrombin-sensitive protein.

An article "The evolving role of thrombospondin-1 (TSP1) in hemostasis and vascular biology" by Bonnefoy et al., Cell. Mol. Life Sci. 65 (2008) 713-727, describes TSP1 as involved in angiogenesis, inflammation, wound healing and hemostasis and further references the structure and domains of the TSP1 as well as the binding of the amino acid (SEQ ID NO: 1) peptide to CD47.

An article "Platelet aggregation induced by the C-terminal peptide of thrombospondin-1 requires the docking protein LAT but is largely independent of alphaIIb/beta3", by Trumel et al., Journal of Thrombosis and Haemostasis, 2003 February; 1(2):320-9, teaches that thrombospondin-1 (TSP1) is abundantly secreted during platelet activation and plays a role in irreversible platelet aggregation. A peptide derived from the C-terminal domain of TSP1, SEQ ID NO: 1 can activate human platelets at least in part via its binding to integrin-associated protein.

An article "Thrombspondin Acts via Integrin-associated Protein to Activate the Platelet Integrin αIIbb3", by Chung et al., J Biol Chem 1997; 272 No. 23, Issue of June 6, pp. 14740-14746, teaches that a peptide from the CBD, SEQ ID NO: 2 (4N1K) has been identified as an IAP agonist. TS1, the CBD, and an IAP agonist peptide (4N1K) from the CBD of TS1 activate the platelet integrin aIIbb3, resulting in platelet spreading on immobilized fibrinogen, stimulation of platelet aggregation, and enhanced tyrosine phosphorylation of focal adhesion kinase.

An article "Thrombospondin promotes platelet aggregation" by Tuszynski et al, Blood, 72, 109-115 (1988), teaches that while the role of TSP in hemostasis is not well understood, it has been postulated that TSP crosslinks platelet-fibrinogen aggregates, stabilizes fibrin clot formation, and modulates fibrinolysis and that a study has suggested that TSP may play a regulatory role in hemostasis by inhibiting platelet adhesion and providing a nonthrombogenic surface.

An article "Thrombospondin-1 acts via IAP/CD47 to synergize with collagen in alpha2beta1-mediated platelet activation", by Chung et al., Blood. 1999 Jul. 15; 94(2): 642-8 describes CD47 agonist peptide, 4N1K (SEQ ID NO: 2), derived from the CBD, synergizes with soluble collagen in aggregating platelet-rich plasma. 4N1K and intact TS1 also induce the aggregation of washed, unstirred platelets on immobilized collagen with a rapid increase in tyrosine phosphorylation.

An article "Stimulation of platelet activation and aggregation by a carboxyl-terminal peptide from thrombospondin binding to the integrin-associated protein receptor", by Dorahy et al., J. Biol Chem 1997; 272:1323-1330, teaches that a peptide from the carboxyl terminus of thrombospondin, SEQ ID NO: 1, directly and specifically induces the activation and aggregation of washed human platelets from different donors at concentrations of 5-25 mM. At lower concentrations the peptide synergizes with suboptimal concentrations of ADP to induce aggregation. Peptide affinity chromatography and immunoprecipitation with a monoclonal antibody were used to identify the receptor for the carboxyl-terminal peptide as the integrin-associated protein. The integrin-associated protein remained bound to the SEQ ID NO: 1 containing peptide column when washed with a scrambled peptide in the presence of 5 mM EDTA, indicating a divalent cation-independent association. It is suggested that integrin-associated protein is the primary receptor for thrombospondin on the surface of resting platelets and is implicated in potentiating the platelet aggregation response.

An article "Thrombospondin-bound integrin-associated protein (CD47) physically and functionally modifies integrin alphaIIbbeta3 by its extracellular domain", by Fujimoto et al., J Biol Chem 2003; 278:26655-26665, teaches that a peptide from the C-terminal cell binding domain, SEQ ID NO: 2 (4N1K) binds to IAP and stimulates the integrin-dependent cell functions, including platelet aggregation. Platelet aggregation induced by 4N1K was not completely inhibited by energy depletion with sodium azide and 2-de-oxy-D-glucose, although ADP or collagen-induced platelet response was completely inhibited.

An article "C-terminal peptide of thrombospondin-1 induces platelet aggregation through the Fc receptor chain-associated signaling pathway and by agglutination" by Tulasne et al., Blood 2001; 98:3346-3352, teaches that a peptide from the C-terminal domain of thrombospondin-1 (Arg-Phe-Tyr-Val-Val-Met-Trp-Lys (SEQ ID NO: 1); known as 4N1-1) has been reported to induce platelet aggregation and to bind to the integrin-associated protein (TAP), which is also known as CD47. It was discovered that 4N1-1 or its derivative peptide, 4N1K, induces rapid phosphorylation of the Fc receptor (FcR) g chain, Syk, SLP-76, and phospholipase C g2 in human platelets. The reference teaches that that the C-terminal peptide of thrombospondin induces platelet aggregation through the FcR g-chain signaling pathway and through agglutination.

An article "The C-terminal peptide of thrombospondin-1 stimulates distinct signaling pathways but induces an activation-independent agglutination of platelets and other cells," by Voit et al., FEBS Letters, 2003; 544: 240-245 teaches that a peptide from the C-terminal domain of thrombospondin-1 (4N1-1) has been proposed to stimulate platelet aggregation by a novel mechanism involving both an activation-independent agglutination and an activation-dependent, glycoprotein (GP) IIb/IIIa-mediated aggregation which involves GPVI signaling but does not involve CD47. The study demonstrates that 4N1-1 stimulated a different pattern of signal transduction pathways than the GPVI agonist convulxin. Furthermore, 4N1-1-induced platelet aggregation was activation-independent and not dependent on GPVI or GPIIb/IIIa. 4N1-1 also stimulated activation-independent agglutination of different megakaryocytic and non-megakaryocytic cells. 4N1-1-induced cell agglutination but not platelet signaling was inhibited by anti-CD47 antibodies.

An article "A model of platelet aggregation involving multiple interactions of thrombospondin-1, fibrinogen, and GPIIbIIIa receptor" by Bonnefoy et al., J Biol Chem 2001; 276:5605-5612, teaches that Thrombospondin-1 (TSP) may, after secretion from platelet a granules, participate in platelet aggregation, but its mode of action is poorly understood. The study evaluated the capacity of TSP to form inter-platelet cross-bridges through its interaction with fibrinogen (Fg), using either Fg-coated beads or Fg bound to the activated GPIIbIIIa integrin (GPIIbIIIa*) immobilized on beads or on activated fixed platelets (AFP), i.e. in a system free of platelet signaling and secretion mechanisms.

U.S. Pat. No. 5,399,667 "Thrombospondin receptor binding peptides" by Frazier et al., teaches novel short peptides that bind to the thrombospondin 1 receptor, which preferably have five amino acid residues which share the tetrapeptide Arg-Val-Ala-Val (SEQ ID NO: 20) and have the specific sequences. The patent further teaches a VVM-containing peptide that binds to the thrombospondin 1 receptor selected from the group consisting of RFYVVMWKQVTQS (SEQ ID NO: 8) (Seq ID No. 1 in '667) and fragments thereof containing at least the sequence SEQ ID NO: 3, and SEQ ID NO: 4 and fragments thereof containing at least the sequence SEQ ID NO: 5.

U.S. Pat. No. 5,190,920 "Method for using synthetic analogs of thrombospondin for inhibiting metastasis activity" to Jacob et al. relates generally to peptide fragments and synthetic analogs of thrombospondin (TSP) which retain thrombospondin-like activity. Compounds and compositions comprising fragments and methods for using synthetic analogs of thrombospondin for promoting or inhibiting thrombospondin-like activity are provided PCT Publication WO 1996/040033 to Thaddeus et al. describes a hemostatic patch composed of a biodegradable matrix, epsilon aminocaproic acids (EACAs), and thrombin receptor activating peptides (TRAPs). The invention discloses many representative embodiments containing gelatin, alginates, oxidized regenerated cellulose, or collagen as a matrix, and EACAs, TRAPs, calcium, RGD peptide, and calcium as active components. Disclosed sequences include SFLLRNPNDKYEPF (SEQ ID NO: 9), SFLLRNPND-KYEP (SEQ ID NO: 10), SFLLRNPNDKYE (SEQ ID NO: 11), SFLLRNPNDKY (SEQ ID NO: 12), SFLLRNPNDK (SEQ ID NO: 13), SFLLRNPND (SEQ ID NO: 14), SFLL-RNPN (SEQ ID NO: 15), SFLLRNP (SEQ ID NO: 16), SFLLRN (SEQ ID NO: 17), SFLLR (SEQ ID NO: 18), SFLL (SEQ ID NO: 19), SFL and their derivatives.

U.S. Pat. No. 7,285,580, "Methods of using primer molecules for enhancing the mechanical performance of tissue adhesives and sealants" to Stedronsky teaches that in addition to the natural proteins various recombinantly-produced proteins may also find use in tissue adhesives and sealants. Not only may the natural proteins described above be recombinantly produced, but also various crosslinkable non-natural recombinant proteins will find use herein. Preferred non-natural recombinantly produced proteins include proteins which comprise repeating units of naturally occurring amino acid sequence blocks from such naturally occurring structural proteins as fibroin, elastin, collagen, keratin, and the like. Preferred repetitive unit proteins for use include SELP8K, SELP0K-CS1 and SELP0K.

PCT Publication WO 2009/040034 "USE OF A PEPTIDE AS A THERAPEUTIC AGENT" to Bevec et al. is directed to the use of the peptide compound Arg-Phe-Tyr-Val-Val-Met-Trp-Lys-OH (SEQ ID NO: 1) as a therapeutic agent for the prophylaxis and/or treatment of cancer, autoimmune diseases, fibrotic diseases, inflammatory diseases, neurodegenerative diseases, infectious diseases, lung diseases, heart and vascular diseases and metabolic diseases and further relates to pharmaceutical compositions preferably in form of a lyophilisate or liquid buffer solution or artificial mother milk formulation or mother milk substitute containing the peptide Arg-Phe-Tyr-Val-Val-Met-Trp-Lys-OH (SEQ ID NO: 1) optionally together with at least one pharmaceutically acceptable carrier, cryoprotectant, lyoprotectant, excipient and/or diluent.

SUMMARY OF THE INVENTION

The present invention is directed to a hemostatic or tissue sealing material having (a) a peptide having a sequence SEQ ID NO: 1 or an amino acid analog sequence thereof, and (b) a scaffold for said peptide or amino acid analogue sequence. The scaffold is preferably hemostatic, such as a natural or genetically engineered absorbable polymer, a synthetic absorbable polymer, or combinations thereof. The natural or genetically engineered absorbable polymers can be selected from the group consisting of a protein, a polysaccharide, or combinations thereof. The protein can be selected from the group consisting of prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents, peptides, or combinations thereof. The polysaccharide can be selected from the group consisting of cellulose, alkyl cellulose, methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid, polyguluronic acid, derivatives of said polysaccharides, or combinations thereof. The synthetic absorbable polymer can be an aliphatic polyester polymer, an aliphatic polyester copolymer, or combinations thereof.

The gelatin can be in the form of an absorbable hemostatic powder matrix, a sponge matrix, a paste matrix, a gel matrix, or combinations thereof. Additionally, the gelatin can be crosslinked and in particle form with a liquid carrier. The liquid carrier can be normal saline solution, wherein gelatin and the peptide(s) are substantially homogenously mixed in combination with the normal saline solution as a liquid phase. The concentration of the peptide in said hemostatic material (powder, sponge, paste or gel) is from about 0.0025 mM to about 1.25 mM. One or more additives or compounds can be incorporated into the hemostatic mixture that is selected from the group consisting of antimicrobial agents, surfactants, antioxidants, humectants, wetting agents, lubricants, thickeners, diluents, and irradiation stabilizers. Further, an extrusion enhancing amount of glycerol can be added.

In one embodiment, the peptide is conjugated to a biocompatible polymer. The biocompatible polymer can be a hydrophilic polymer, such as polyethylene glycol, a derivative of the polyethylene glycol, polypropylene glycol, polysaccharide, modified polysaccharide, protein, modified protein, peptide, polylactide glycolide, caprolactone, trimethylene carbonate, starch, modified starch, gelatin, collagen, or combinations thereof.

In an alternative embodiment, the hydrophilic polymer is a polyethylene glycol having a molecular weight that has been selected to provide for a rapid hemostasis or for a rapid tissue sealing. The polyethylene glycol molecule can be a linear molecule, a branched molecule, a star-shaped molecule, or combinations thereof. The molecular weight can be on average from about 1000 Daltons to about 8000 Daltons, preferably said molecular weight is on average 2000 or 5000 Daltons.

In an alternative embodiment, the hemostatic or tissue sealing material of contains an amino acid analog sequence that is obtained from sequence SEQ ID NO: 1 wherein at least one the amino acids is substituted with corresponding analog amino acids. The amino acid analog sequence can be selected from the group consisting of SEQ ID NO: 2, SEQ ID NO: 3, SEQ ID NO: 4, SEQ ID NO: 5, and combinations thereof.

The present invention also relates to a method of providing a hemostatic treatment or tissue sealing to a wound site, comprising the steps of: (a) forming the hemostatic or tissue sealing material as described above, and (b) applying the hemostatic or tissue sealing material to the wound site.

The present invention also relates to a method of making a hemostatic or tissue sealing material comprising the steps of: (a) providing a peptide having a sequence SEQ ID NO: 1 or an amino acid analog sequence thereof, said peptide optionally conjugated to a polyethylene glycol; (b) providing an absorbable scaffold; and (c) mixing said peptide and said absorbable scaffold substantially homogenously forming the hemostatic or tissue sealing material.

In one embodiment, the hemostatic material or tissue sealing material and methods described above are used on a patient having heparinized blood or otherwise containing anti-clotting or anti-coagulant agents.

DETAILED DESCRIPTION OF THE INVENTION

Figure 1:
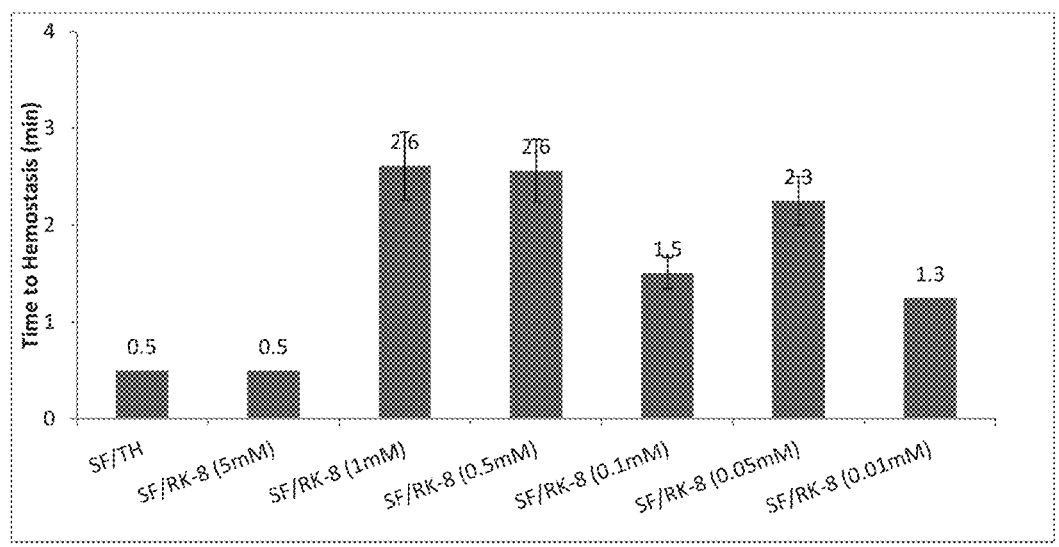
FIG. 1 shows data on time to hemostasis for several tested systems.

Amino acids and peptides are commonly abbreviated as shown below:

| Trivial name | Symbols | | Systematic name | Formula |
| --- | --- | --- | --- | --- |
| Alanine | Ala | A | 2-Aminopropanoic acid | $CH_3$—$CH(NH_2)$—COOH |
| Arginine | Arg | R | 2-Amino-5-guanidinopentanoic acid | $H_2N$—C(=NH)—NH—$[CH_2]_3$—$CH(NH_2)$—COOH |
| Asparagine | Asn | N | 2-Amino-3-carbamoylpropanoic acid | $H_2N$—CO—$CH_2$—$CH(NH_2)$—COOH |
| Aspartic acid | Asp | D | 2-Aminobutanedioic acid | HOOC—$CH_2$—$CH(NH_2)$—COOH |
| Cysteine | Cys | C | 2-Amino-3-mercaptopropanoic acid | HS—$CH_2$—$CH(NH_2)$—COOH |

| Trivial name | Symbols | | Systematic name | Formula |
|---|---|---|---|---|
| Glutamine | Gln | Q | 2-Amino-4-carbamoylbutanoic acid | $H_2N-CO-[CH_2]_2-CH(NH_2)-COOH$ |
| Glutamic acid | Glu | E | 2-Aminopentanedioic acid | $HOOC-[CH_2]_2-CH(NH_2)-COOH$ |
| Glycine | Gly | G | Aminoethanoic acid | $CH_2(NH_2)-COOH$ |
| Histidine | His | H | 2-Amino-3-(1H-imidazol-4-yl)-propanoic acid | |
| Isoleucine | Ile | I | 2-Amino-3-methylpentanoic acid | $C_2H_5-CH(CH_3)-CH(NH_2)-COOH$ |
| Leucine | Leu | L | 2-Amino-4-methylpentanoic acid | $(CH_3)_2CH-CH_2-CH(NH_2)-COOH$ |
| Lysine | Lys | K | 2,6-Diaminohexanoic acid | $H_2N-[CH_2]_4-CH(NH_2)-COOH$ |
| Methionine | Met | M | 2-Amino-4-(methylthio)butanoic acid | $CH_3-S-[CH_2]_2-CH(NH_2)-COOH$ |
| Phenylalanine | Phe | F | 2-Amino-3-phenylpropanoic acid | $C_6H_5-CH_2-CH(NH_2)-COOH$ |
| Proline | Pro | P | Pyrrolidine-2-carboxylic acid | |
| Serine | Ser | S | 2-Amino-3-hydroxypropanoic acid | $HO-CH_2-CH(NH_2)-COOH$ |
| Threonine | Thr | T | 2-Amino-3-hydroxybutanoic acid | $CH_3-CH(OH)-CH(NH_2)-COOH$ |
| Tryptophan | Trp | W | 2-Amino-3-(1H-indol-3-yl)-propanoic acid | |
| Tyrosine | Tyr | Y | 2-Amino-3-(4-hydroxyphenyl)-propanoic acid | |
| Valine | Val | V | 2-Amino-3-methylbutanoic acid | $(CH_3)_2CH-CH(NH_2)-COOH$ |

According to an embodiment of the present invention, an 8-amino acid peptide having a sequence RFYVVMWK (Arg-Phe-Tyr-Val-Val-Met-Trp-Lys (SEQ ID NO: 1)), also referred to herein as RK-8, (optionally PEG-conjugated or pegylated) which can be derived from human protein TSP-1, was found to have strong hemostatic properties and/or tissue sealing properties when used in combination with a scaffold, preferably a hemostatic scaffold material.

Preferred hemostatic scaffolds are natural or genetically engineered absorbable polymers or synthetic absorbable polymers, or mixtures thereof. Examples of natural or genetically engineered absorbable polymers are proteins, polysaccharides and combinations thereof. Proteins include, prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents, synthetic peptides having hemostatic activity, and/or combinations thereof. Polysaccharides include, without limitation, cellulose, alkyl cellulose, e.g. methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyguluronic acid, and derivatives of any of the above. Examples of synthetic absorbable polymers are aliphatic polyester polymers, copolymers, and/or combinations thereof. The aliphatic polyesters are typically synthesized in a ring opening polymerization of monomers including, but not limited to, lactic acid, lactide (including L-, D-, meso and D, L mixtures), glycolic acid, glycolide, ϵ-caprolactone, p-dioxanone (1,4-dioxan-2-one), and trimethylene carbonate (1,3-dioxan-2-one). In one embodiment, the natural absorbable polymer is gelatin, such as SURGIFLO™ available from Ethicon, Inc, which is a crosslinked gelatin in particle form that is combined with a liquid carrier and a gas component in a delivery device, such as a syringe.

In one embodiment, an amino acid analog sequence is used whereby at least one amino acid in the SEQ ID NO: 1 sequence has been substituted with analog or bio-similar amino-acids. A table of analog or bio-similar amino acids is provided below:

| Trivial name | Symbols | | Analog or BioSimilar Amino Acids |
|---|---|---|---|
| Arginine | Arg | R | His (H), Lys (K) |
| Lysine | Lys | K | Arg (R), His (H) |
| Methionine | Met | M | Ala (A), Ile (I), Leu (L), Phe (F), Trp (W), Tyr (Y), Val (V), Cys (C), Ser (S) |
| Tryptophan | Trp | W | Ala (A), Ile (I), Leu (L), Phe (F), Met (M), Tyr (Y), Val (V), His (H) |
| Tyrosine | Tyr | Y | Ala (A), Ile (I), Leu (L), Phe (F), Met (M), Trp (W), Val (V), His (H) |
| Valine | Val | V | Ala (A), Ile (I), Leu (L), Phe (F), Met (M), Trp (W), Val (V) |
| Phenylalanine | Phe | F | Trp (W), Tyr (Y), His (H), Ile (I), Leu (L) |

The amino acids can be in L, D form, or their derivatives [e.g. pseudo amino acid, functionalized amino acid (e.g. fluorinated amino acid . . . etc), beta amino acid, gamma amino acid . . . etc]. Examples of the particularly preferred analog peptides to the SEQ ID NO: 1 peptide sequence are:

KRFYVVMWKK
(Lys-Arg-Phe-Tyr-Val-Val-Met-

Trp-Lys-Lys (SEQ ID NO: 2))

RFYVVM
(Arg-Phe-Tyr-Val-Val-Met (SEQ ID NO: 3))

FIRVVMYEGKK
(Phe-Ile-Arg-Val-Val-Met-Tyr-

Glu-Gly-Lys-Lys (SEQ ID NO: 4))

IRVVM
(Ile-Arg-Val-Val-Met (SEQ ID NO: 5))

According to an embodiment of the present invention the peptide is optionally conjugated to a biocompatible polymer, more preferably to a hydrophilic polymer. The hydrophilic polymer can be polyethylene glycol, derivatives of the polyethylene glycol, polypropylene glycol, polysaccharide, modified polysaccharide, protein, modified protein, polypeptide, polylactide glycolide, caprolactone, or trimethylene carbonate, and/or combinations thereof.

According to an embodiment of the present invention, amino peptides containing the SEQ ID NO: 1 sequence for hemostasis that are combined with scaffolding (such as gelatin) provide for the following advantages: Low molecular weights peptides, such as SEQ ID NO: 1, are more stable than large proteinaceous hemostatic agents, such as thrombin and may be stored without refrigeration. Large-scale manufacture of the peptides can be done by recombinant DNA technology or chemical peptide synthesis with both methods being more cost effective than purification of biologics (e.g., thrombin). The amino peptide SEQ ID NO: 1 and analog peptides that are conjugated with PEG advantageously have improved solubility of the peptide. Further, it was discovered that pegylated peptides are more effective at lower concentrations for hemostasis and work well in heparinized blood.

The present invention further relates to a method of providing a hemostatic treatment to a bleeding site, comprising the steps of forming a hemostatic preparation described above, and applying the hemostatic preparation to the bleeding site.

The present invention further relates to a method of making a semi-liquid hemostatic preparation comprising the steps of mixing the hemostatic matrix with the hemostasis-promoting agent containing the SEQ ID NO: 1 amino acid peptide and/or an amino acid analog sequence thereof, and applying the resulting material to a wound site.

Description of gelatin carriers. The gelatin material of the present invention is preferably a liquid permeable, water insoluble gelatin based sponge or paste. Gelatin, which is a denatured form of the protein collagen, has been used in a variety of wound dressings. Since gelatin gels have a relatively low melting point, they are not very stable at body temperature. Therefore, it is imperative to stabilize these gels by establishing cross-links between the protein chains. In practice, this is usually obtained by treating the gelatin with glutaraldehyde or formaldehyde or heat. Thus cross-linked gelatin may be fabricated into dry sponges which are useful for inducing hemostasis in bleeding wounds or ground into particulate form.

The term "gel" is used herein to denote a swollen, hydrated polymer network which is essentially continuous throughout its volume. A protein gel is composed of an essentially continuous network of linked protein molecules and a liquid (typically aqueous) solvent, which fills the space within the protein matrix. The protein matrix exerts a strong viscous drag on the solvent molecules, preventing them from flowing freely. The component molecules making up the gel network may be linked by ionic, hydrophobic, metallic or covalent bonds. The covalent bond is the most thermally stable of these bonds.

In one embodiment, sterilized compositions of the present invention can contain solid, porous or non-porous particles of a biocompatible polymer suitable for use in hemostasis, a biocompatible liquid and the hemostatic extract as described above as its three primary components. Particles, liquid and hemostatic extract are combined and mixed under conditions effective to provide a substantially homogeneous hemostatic composition comprising a continuous liquid phase comprising the hemostatic extract and having the solid polymer particles homogenously dispersed there through. The amount and average diameter of particles contained in the composition and the relative amounts of the solid, liquid and hemostatic extract is effective to provide the composition with hemostatic and physical properties, as described herein below.

As used herein, "continuous" and "discontinuous" are used in the ordinary meaning of those words in the context of standard nomenclature used to define and describe dispersions.

As used herein, "substantially homogenous" denotes that physical state of the compositions or pastes where the solid particles are uniformly dispersed throughout the continuous liquid phase such that the ratio of solid:liquid and the density of any portion or cross-section of the composition or paste are substantially the same.

As used herein, "sterile" means substantially free of living germs and/or microorganisms and as further recognized and described by governmental standards pertaining to compositions and medical devices described and claimed herein.

As used herein, "hemostatic", or "hemostatic properties", means the ability to stop or minimize bleeding, as one skilled in the art of hemostasis would understand those terms to mean, as further exemplified in the examples of the specification.

A variety of biocompatible natural, semi-synthetic or synthetic polymers may be used to prepare the solid particles used in compositions of the present invention. The polymer selected must be substantially insoluble in the liquid chosen for the particular composition. Preferably, water-insoluble biodegradable polymers that provide mechanical, chemical and/or biological hemostatic activity are used. Polymers that may be used include, without limitation, proteins and polysaccharides. Polysaccharides that may be used include oxidized cellulose, chitosan, chitin, alginate, oxidized alginate and oxidized starch. The biocompatible polymer used to prepare the particles preferably is a cross-linked or denatured protein, such as gelatin, collagen, fibrinogen or fibronectin. A preferred gelatin powder is a partially cross-linked gelatin powder prepared by milling gelatin sponge into particles having an average diameter of from about 40 microns to about 1200 microns, more preferably from about 100 microns to about 1000 microns, as determined by laser diffraction.

Sterile compositions of the present invention preferably comprise a continuous liquid phase in which the hemostatic extract and solid gelatin-based particles are dispersed. Depending upon the particular medical device and use thereof, the liquid may be aqueous or non aqueous. Preferably, the liquid phase is aqueous. Aqueous liquids may include, without limitation, biocompatible aqueous solutions, such as calcium chloride and saline. More preferably, the liquid phase comprises saline. The liquid phase and solid particulate phase are present in relative amounts effective to provide a composition, for example a paste, or slurry, suitable for use in providing hemostasis. In certain embodiments, the weight ratio of solid particles to liquid generally is from about 1:1 to about 1:12, or from about 1:3 to about 1:8 or even about 1:5.

The hemostatic compositions may further comprise effective amounts of one or more additives or compounds including, but not limited to, antimicrobial agents, surfactants, antioxidants, humectants, wetting agents, lubricants, thickeners, diluents, irradiation stabilizers, e.g. radical scavengers, plasticizers, and stabilizers. For example, glycerol may be added to enhance the extrudability or injectability of the composition. When utilized, glycerol may be present in the compositions at from about 0% to about 20% by weight, based on the weight of the liquid phase. Preferably, the composition may comprise from about 1% to about 10% by weight of glycerol, based on the weight of the liquid phase. More preferably, the compositions may comprise from about 1% to about 5% by weight of glycerol, based on the weight of the liquid phase.

In addition, quaternary amines may be used to provide enhanced properties to the compositions. For example, benzalkonium chloride, Polybrene or Onamer M may be used at levels up to about 1 percent by weight, based on the weight of the liquid phase. Preferably, benzalkonium chloride is used at levels of from about 0.001% to about 0.01% by weight, based on the weight of the liquid phase. More preferably, the compositions may comprise from about 0.002 to about 0.006% by weight benzalkonium chloride, based on the weight of the liquid phase. It is believed that the quaternary amines may serve multiple functions, acting as an antimicrobial agent, a foaming agent, a radical scavenger and as a heparin neutralizer.

The hemostatic preparation can further contain effective amounts of one or more additives or compounds selected from the group consisting of antimicrobial agents, surfactants, antioxidants, humectants, wetting agents, lubricants, thickeners, diluents, irradiation stabilizers, e.g. radical scavengers, plasticizers, and stabilizers, more particularly including an extrusion enhancing amount of glycerol, and preferably wherein the glycerol is present at an amount from about 1% to about 20% by weight, based on the weight of the liquid phase of the overall hemostatic preparation.

Such hemostatic compositions may further comprise heparin neutralizers, additional procoagulants or hemostatic agents, such as fibrinogen, fibrin, Factor Xa, or Factor VIIa. By "effective amount", it is meant that amount necessary to provide to the compositions those properties for which the additive is being added. The effective amount also is limited by the maximum amount that may be added without causing detrimental biological effects.

Methods for incorporating peptides onto gelatin carriers. In one embodiment for making compositions of the invention, a substantially homogenous paste is prepared by mixing the particles with the liquid to form a uniform paste. The liquid includes the hemostatic peptide material and may include effective amounts of other additives dissolved therein as described above. Mixing may be accomplished by extrusion or by mixing in a confined space under conditions effective to provide a uniform dispersion of the solid particles in the liquid phase. Alternately, a mixer, e.g. a double planetary mixer, may be utilized in making compositions of the present invention. The liquid containing the hemostatic peptide material is added to the mixer. The liquid may include effective amounts of additives dissolved therein prior to addition of particles to the solution. For example, a saline solution containing hemostatic peptide material, glycerol and benzalkonium chloride may be prepared and then added to the mixer. The solid particles are added to the mixer over time with continuous mixing until all ingredients have been added. The mixing is continued until such time as a substantially homogenous composition is formed containing the solid particles uniformly dispersed throughout the continuous liquid phase.

In an alternative embodiment, the hemostatic peptide is applied by spraying or printing upon a major surface of substantially dry sponge.

The hemostatic compositions prepared as above can be sterilized to provide sterile compositions comprising the hemostatic peptide. In some embodiments the compositions are transferred into a medical device as described above and the device containing the hemostatic composition is sterilized, preferably by ionizing radiation. More preferably, sterilization is by gamma irradiation as exemplified herein.

Compositions of the present invention include compositions described herein that are sterile, in that they have been irradiated with a level of, e.g. ionizing irradiation. Such irradiation may include e-beam or gamma irradiation. The level of irradiation and conditions of sterilization, including the time that the compositions are irradiated, are those that provide sterile compositions, as defined herein. Once having the benefit of this disclosure, one skilled in the art will be able to readily determine the level of irradiation necessary to provide sterile compositions.

Medical devices in which the hemostatic compositions of the present invention may be utilized include any device currently being used to apply a flowable or injectable hemostatic paste or slurry to a site, or wound, requiring hemostasis. A sponge can be applied by hand or other means in conventional fashion. The site requiring hemostasis may be the result of an injury or a surgical procedure. Examples of devices or applicators include syringes such as Becton Dickinson or Monoject luer syringes. Other devices are disclosed in detail in U.S. Pat. No. 6,045,570, the contents of which are incorporated by reference in their entirety.

Synthetic peptides of varying sequences were synthesized with Fmoc-mediated solid supported peptide synthesis. PEG-conjugated peptides, PEG2000-RK-8 or PEG5000-RK-8, designated as P2K-RK-8 or P5K-RK-8, respectively, were synthesized by conjugating methoxypolyethylene glycol-N-hydroxysuccinimide (mPEG-NHS) onto the N-terminus of purified SEQ ID NO: 1 via solution synthesis. The peptides were purified by C18 RP-HPLC to give >95% purity. Their identities were analyzed by MALDI-TOF MS or ESI-MS.

The mixtures with Surgiflo™, which is a gelatin based hemostatic matrix were prepared as follows. Test articles included mixtures of gelatin based Surgiflo™ with 2 mL of normal saline or 2 mL of normal saline containing active component or such as SEQ ID NO: 1, pegylated SEQ ID NO: 1, or its analog; or 2 mL EVITHROM™ solution containing primarily human thrombin (full composition of Evithrom® contains human thrombin (800-1200 IU/mL), calcium chloride, human albumin, mannitol, sodium acetate, and water for injection).

For testing article preparation, Surgiflo™ was thoroughly mixed with the hemostatic material by the following steps: 1. Draw 2 mL of hemostatic material solution such as saline or saline with peptide into an empty syringe; 2. Mix the 2 components by attaching a luer connector to a pre-filled syringe and attaching the hemostatic material solution-containing syringe to the other end of the luer adapter, and then inject the hemostatic material solution into a pre-filled syringe; 3. Continue to mix the components by pushing the combined material back and forth until the consistency is even, and apply to the wound.

All concentrations in the examples and charts refer to concentration in 2 mL saline prior to mixing with 6 mL Surgiflo™. Upon mixing the concentration of the active ingredient or excipient in the test article will correspond to ¼ of the concentration in the saline solution; For example 5 mM concentration as referred in the examples corresponds to final concentration of 0.25×5 mM=1.25 mM in the hemostatic material.

In the figures the SF stands for Surgiflo™ Hemostatic Matrix; and TH stands for EVITHROM™, available from Ethicon, Inc., containing Thrombin Topical (human), 800~1200 IU/mL.

While the following examples demonstrate certain embodiments of the invention, they are not to be interpreted as limiting the scope of the invention, but rather as contributing to a complete description of the invention.

EXAMPLE 1

Referring now to FIG. 1, data on time to hemostasis in minutes is presented for several tested systems, all including Surgiflo™, (designated on the chart as SF), and different types of additives for improved hemostasis, including human thrombin (designated as TH on the chart) and synthetic peptide SEQ ID NO: 1 having concentration varying from 0.01 mM to 5 mM. The mixtures of Surgiflo™ with thrombin are designated on the chart as SF/TH; the mixtures of Surgiflo™ with SEQ ID NO: 1 are designated on the chart as SF/RK-8.

The data was collected using porcine liver biopsy punch model [8 mm wide×7 mm deep], with Initial tamponade time: 30 s; observation time: 30 s; N is number of experiments for each data point; N=3. The error bars on the charts correspond to standard deviations.

In vivo hemostatic activity study was performed using the porcine porcine liver biopsy punch model, with the punched wound opening 8 mm wide×7 mm deep made on the liver and the test article applied to a freshly created wound site followed by an occlusive digital pressure (tamponade). Pressure was initially applied for 30 seconds and was timed using an electronic timer. Following the 30 seconds tamponade, digital pressure was discontinued; the gauze pad on the article was immediately removed. A 30-second hemostasis evaluation period was performed. If free flow bleeding was not observed within 30 seconds, the time to hemostasis was noted, in a minutes seconds format, and testing was concluded for that article. If free flow bleeding was observed, pressure and gauze were reapplied for additional 30 second tamponade and observation periods until hemostasis was achieved or until the testing period reached ten minutes. Hemostasis was determined by the cessation of free flow bleeding in less than ten minutes. Gauze pad was used as a negative control.

As can be seen from FIG. 1, Surgiflo™ mixture with the higher concentration of SEQ ID NO: 1 (5 mM) has similar efficacy to Surgiflo™/Thrombin (SF/TH) mixture, indicating a strong hemostatic effect of the SEQ ID NO: 1 peptide.

EXAMPLE 2

Figure 2:
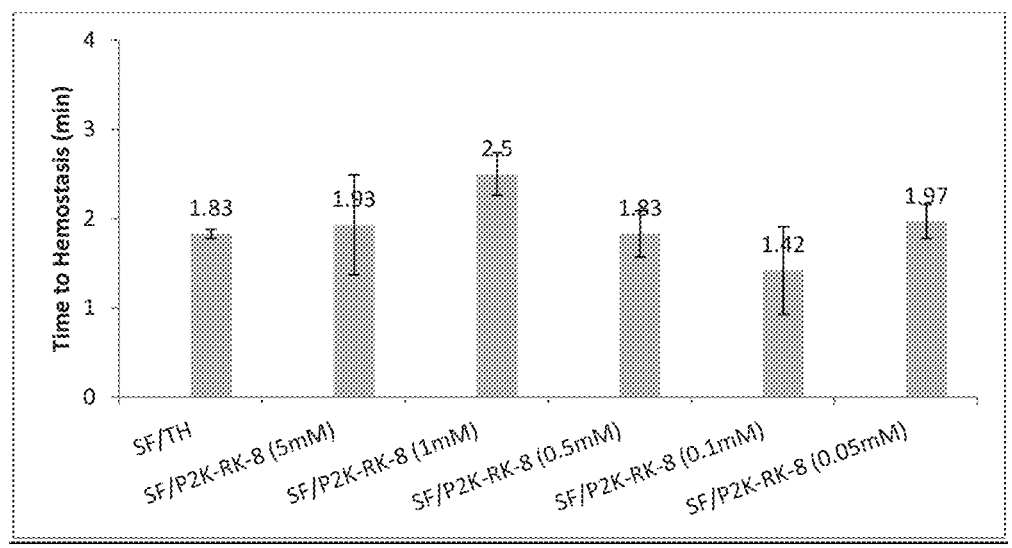
FIG. 2 shows data on time to hemostasis for several tested systems.

Referring now to FIG. 2, data on time to hemostasis in minutes is presented for several tested systems, all including Surgiflo™, (designated on the chart as SF), and different types of additives for improved hemostasis, including human thrombin (designated as TH on the chart) and PEG-conjugated (or pegylated) synthetic peptide SEQ ID NO: 1. For PEG-conjugation, PEG2000 or polyethylene glycol with the average molecular weight of 2000 Da was used, designated on the chart as P2K. The mixture of pegylated SEQ ID NO: 1 and Surgiflo™ is designated on the chart as SF/P2K-RK-8. This mixture was tested with the concentration of SEQ ID NO: 1 varying from 0.05 mM to 5 mM.

The data was collected using in vivo porcine spleen biopsy punch model [6 mm wide×3 mm deep], initial tamponade time: 30 s; observation time: 30 s; N=3.

In vivo hemostatic activity study was performed using the porcine spleen biopsy punch model, with the punched wound opening 6 mm wide×3 mm deep made on the spleen and the test article applied to a freshly created wound site followed by an occlusive digital pressure (tamponade). Pressure was initially applied for 30 second and was timed using an electronic timer. Following the 30 seconds tamponade, digital pressure was discontinued; the gauze pad on the article was immediately removed. A 30-second hemostasis evaluation period was performed. If free flow bleeding was not observed within 30 seconds, the time to hemostasis was noted, in a minutes seconds format, and testing was concluded for that article. If free flow bleeding was observed, pressure and gauze were reapplied for additional 30 seconds tamponade and observation periods until hemostasis was achieved or until the testing period reached ten minutes. Hemostasis was determined by the cessation of free flow bleeding in less than ten minutes. Gauze pad was used as a negative control.

As can be seen from FIG. 2, in mixtures with Surgiflo™, pegylated SEQ ID NO: 1 is comparable to thrombin over a wide range of concentrations varying from 0.05 mM to 5 mM, showing practically the same time to hemostasis as Thrombin and possibly better time to hemostasis than Thrombin at 0.1 mM concentration of pegylated SEQ ID NO: 1.

EXAMPLE 3

Figure 3:
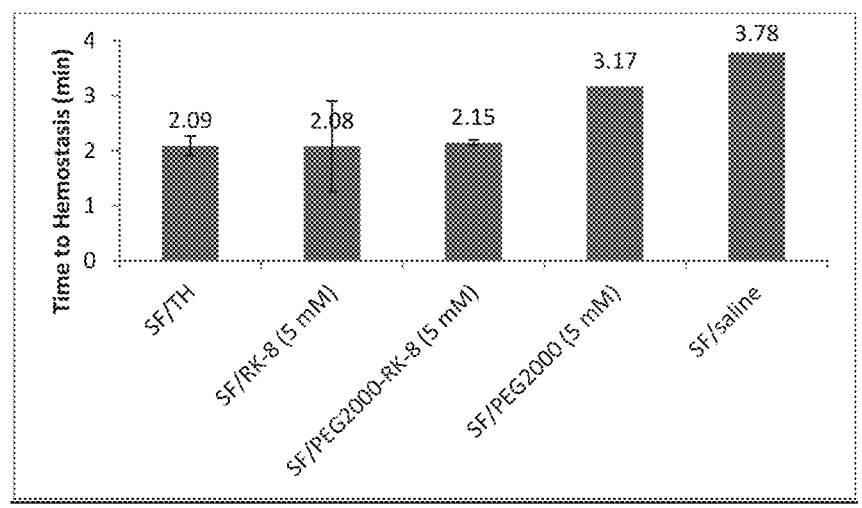
FIG. 3 shows data on time to hemostasis for several tested systems.

Referring now to FIG. 3, data on time to hemostasis in minutes is presented for several tested systems, all including Surgiflo™, (designated on the chart as SF), and different types of controls or additives for improved hemostasis, including: human thrombin (designated as SF/TH); SEQ ID NO: 1 peptide (designated as SF/RK-8), having concentration of 5 mM; SEQ ID NO: 1 conjugated with PEG 2000 (designated on the chart as SF/PEG2000-RK8) having concentration of 5 mM; PEG-2000 (designated on the chart as SF/PEG2000) having concentration of 5 mM; and normal saline (designated on the chart as SF/saline).

The data was collected using porcine spleen biopsy punch model [6 mm wide×3 mm deep], initial tamponade time: 30 s; observation time: 30 s; N=3.

As can be seen from FIG. 3, direct comparison of mixtures of Surgiflo™ with SEQ ID NO: 1 and with pegylated SEQ ID NO: 1 to mixtures with thrombin and to controls representing mixtures with non-hemostasis inducing excipients, represented by PEG2000 and normal saline, indicates that mixtures of Surgiflo™ with pegylated SEQ ID NO: 1 (5 mM) and with SEQ ID NO: 1 (5 mM) showed similar hemostatic efficacy to mixtures with thrombin. Mixtures of Surgiflo™ with pegylated SEQ ID NO: 1 or with SEQ ID NO: 1 demonstrated much faster time to hemostasis vs. mixtures of Surgiflo™ with saline and with PEG2000 (5 mM).

EXAMPLE 4

Figure 4:
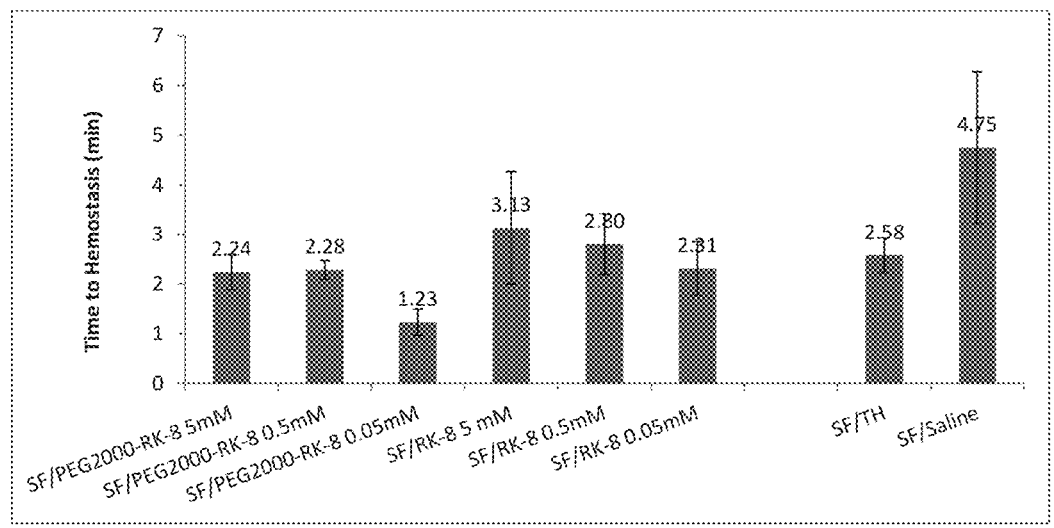
FIG. 4 shows data on time to hemostasis for several tested systems.

Referring now to FIG. 4, data on time to hemostasis in minutes is presented for several tested systems, all including Surgiflo™, (designated on the chart as SF), and different types of controls or additives at variable concentrations for improved hemostasis, including:

SEQ ID NO: 1 conjugated with PEG 2000 (designated on the chart as SF/PEG2000-RK8) having concentrations of 0.05-5 mM;

SEQ ID NO: 1 peptide (designated as SF/RK-8), having concentrations of 0.05-5 mM Control: Surgiflo™ with human thrombin (designated as SF/TH);

Control: Surgiflo™ with normal saline (designated on the chart as SF/saline).

The data was collected using porcine spleen biopsy punch model [6 mm wide×3 mm wide], initial tamponade time: 30 s; observation time: 30 s; N=3.

As can be seen from FIG. 4, direct comparison of mixtures of Surgiflo™ with SEQ ID NO: 1 and pegylated SEQ ID NO: 1 to mixtures with thrombin and with normal saline, indicates that mixtures of Surgiflo™ with pegylated SEQ ID NO: 1 showed better or similar hemostatic efficacy vs. mixtures of Surgiflo™ with thrombin at all concentrations, with particularly fast time to hemostasis at 0.05 mM of pegylated SEQ ID NO: 1. Further, mixtures of Surgiflo™ with SEQ ID NO: 1 showed hemostatic efficacy comparable to mixtures of Surgiflo™ with thrombin. In all cases, the hemostatic efficacy was better vs. mixtures of Surgiflo™ with saline. Further analysis indicates that pegylated SEQ ID NO: 1 showed better hemostatic efficacy than SEQ ID NO: 1 and Thrombin in mixtures with Surgiflo™.

EXAMPLE 5

Figure 5:
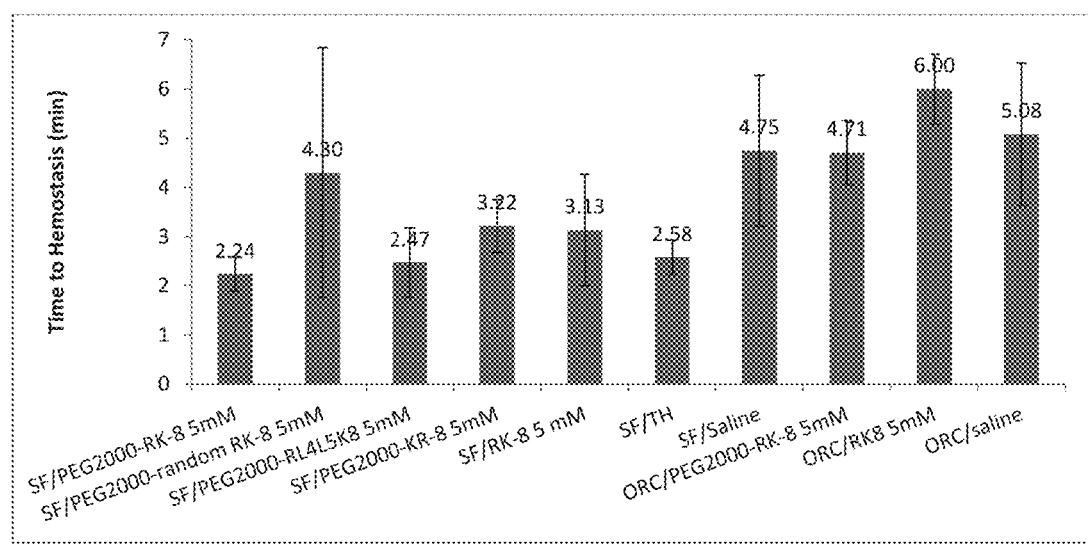
FIG. 5 shows data on time to hemostasis for several tested systems.

Referring now to FIG. 5, data on time to hemostasis in minutes is presented for several tested systems, based on two different hemostatic scaffolds, including Surgiflo™, (designated on the chart as SF), and scaffold made of oxidized regenerated cellulose, or ORC powder (designated on the chart as ORC).

Oxidized regenerated cellulose (ORC) is a known and widely used hemostat, available from Ethicon, Inc. as SURGICEL Original, SURGICEL Nu-Knit, SURGICEL Fibrillar, and SURGICEL SNoW. ORC powder was prepared by milling of ORC fabric and then intermixing the resulting powder with normal saline and or with the corresponding peptide.

The inventors have tested the following ORC-based compositions:
mixtures of ORC with pegylated SEQ ID NO: 1 at 5 mM concentration (designated on the chart as ORC/PEG2000-RK-8)
mixtures of ORC with SEQ ID NO: 1 at 5 mM concentration (designated on the chart as ORC/RK-8)
mixtures of ORC with normal saline The data was collected using porcine spleen biopsy punch model [6 mm wide×3 mm wide], initial tamponade time: 30 s; observation time: 30 s; N=4.

Comparison with controls indicates that all ORC-based compositions performed as hemostats comparable with Surgiflo™ with normal saline (designated on the chart as SF/saline) and had longer time to hemostasis vs. Surgiflo™ with human thrombin (designated as SF/TH). Thus ORC-based hemostatic scaffold is not suitable for use with SEQ ID NO: 1 and or pegylated SEQ ID NO: 1.

FIG. 5 further illustrates data obtained using Surgiflo™ mixtures with pegylated SEQ ID NO: 1 and pegylated SEQ ID NO: 1 like 8 amino acid peptides with varying sequences at concentrations of 5 mM. Referring now to Table 1, sequences of SEQ ID NO: 1 and three SEQ ID NO: 1 like 8 amino acid peptides are presented, along with the abbreviated designation on the chart. All peptides including SEQ ID NO: 1 were pegylated.

TABLE 1

| Peptide sequences | |
|---|---|
| Designation on the chart | Conjugation and Sequence |
| PEG2000-RK-8 | PEG2000-SEQ ID NO: 1 |
| PEG2000-random RK-8 | PEG2000-KVYRWFMV (SEQ ID NO: 21) |
| PEG2000-RL4L5K8 | PEG2000-SEQ ID NO: 6 |
| PEG2000-KR-8 | PEG2000-SEQ ID NO: 7 |

8 amino acid peptide PEG2000-KVYRWFMV (SEQ ID NO: 21) or PEG2000-random RK-8 has a random sequence KVYRWFMV (SEQ ID NO: 21);

8 amino acid peptide PEG2000-RL4L5K8 or PEG2000-SEQ ID NO: 6 has a sequence RFYLLMWK ((Arg-Phe-Tyr-Leu-Leu-Met-Trp-Lys) SEQ ID NO: 6)) analog to RK-8 but with VVM substituted for LLM, whereby V and L are analog amino acids.

8 amino acid peptide PEG2000-KR-8 or PEG2000-SEQ ID NO: 7 has a sequence KYFLLQFR ((Lys-Tyr-Phe-Leu-Leu-Gln-Phe-Arg) SEQ ID NO: 7)), where each individual amino acid of RK-8 is substituted with an analog amino acid but with different side chain.

Analysis of the data indicates that 8 amino acid pegylated peptide having RK-8-like sequence, particularly SEQ ID NO: 6 showed similar hemostatic efficacy compared to pegylated SEQ ID NO: 1 and to thrombin.

The pegylated 8 amino acid peptide SEQ ID NO: 7 showed somewhat longer time to hemostasis, comparable to non-pegylated SEQ ID NO: 1.

The pegylated random sequence 8 amino acid peptide KVYRWFMV (SEQ ID NO: 21) showed longer time to hemostasis, comparable to SF/saline mixture.

EXAMPLE 6

Figure 6:
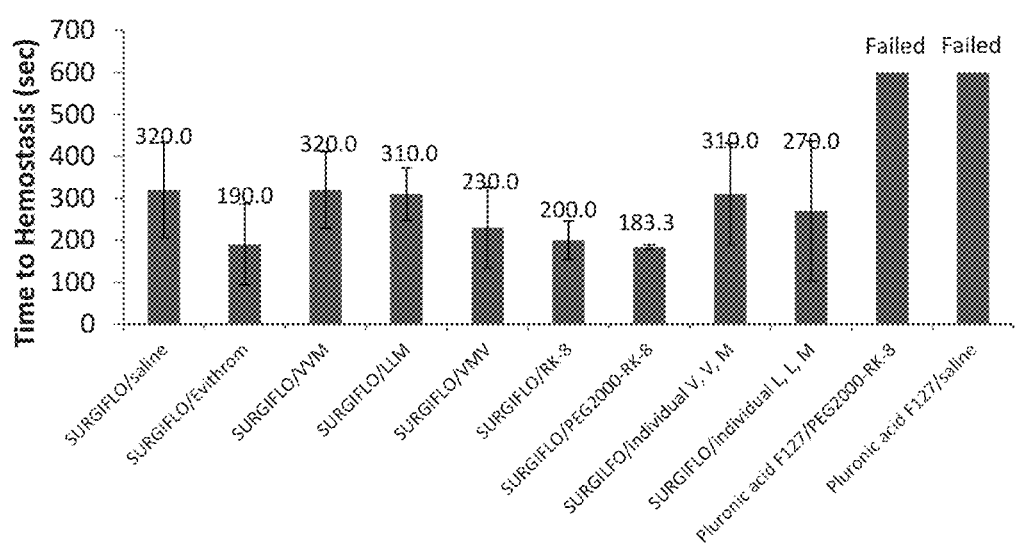
FIG. 6 shows data on time to hemostasis for several tested systems.

Referring now to FIG. 6, data on time to hemostasis in seconds is presented for several tested systems, based on two different hemostatic scaffolds, including Surgiflo™, (designated on the chart as Surgiflo), and scaffold made of Pluronic acid F127 (designated on the chart as Pluronic acid F127).

Pluronic acid F127 is (PPO)x-(PEO)y block copolymer, having average molecular weight of 12600 Da. It was purchased from BASF and prepared as follows: 0.58 g of Pluronic acid F127 was mixed with 2 mL of saline or saline containing 5 mM pegylated PR-8.

The data was collected using porcine spleen biopsy punch model [6 mm wide×3 mm deep], initial tamponade time: 30 s; observation time: 30 s.

Analysis of the data indicates that mixtures of Pluronic acid with pegylated RK-8 and with normal saline have failed in hemostatic testing. Thus Pluronic acid based compositions performed poorly as hemostats and are not suitable for use with pegylated RK-8.

FIG. 6 also presents data obtained with Surgiflo™ mixtures with saline (designated Surgiflo/Saline) and with Evithrom™ (human thrombin, Thrombin Topical (human), 800~1200 IU/mL) (designated as Surgiflo/Evithrom) as controls, as well as Surgiflo™ mixtures with:

Short 3-amino acids peptides having sequences VVM, LLM, VMV, having concentration 5 mM (designated on the chart as Surgiflo/VVM; Surgiflo/LLM; Surgiflo/VMV)

SEQ ID NO: 1 peptide (designated as Surgiflo/RK-8), having concentration of 5 mM SEQ ID NO: 1 conjugated with PEG 2000 (designated on the chart as Surgiflo/PEG2000-RK8) having concentration of 5 mM Mixture of three individual amino acids V, V, M; (designated on the chart as Surgiflo/individual V,V,M) having concentration of 5 mM each)

Mixture of three individual amino acids L, L, M; (designated on the chart as Surgiflo/individual L,L,M) having concentration of 5 mM each)

3-amino-acid peptides, VVM, LLM, and VMV, were synthesized by GenScript USA Inc.

Analysis of the data presented in FIG. 6 indicates that mixtures of Surgiflo™ with individual amino acids and short 3-amino acids peptides were not effective as hemostatic agents, with the exception of VMV peptide which was somewhat effective.

Further analysis of the data shows that SEQ ID NO: 1 and PEG-SEQ ID NO: 1 performed as well as thrombin.

EXAMPLE 7

Figure 7:
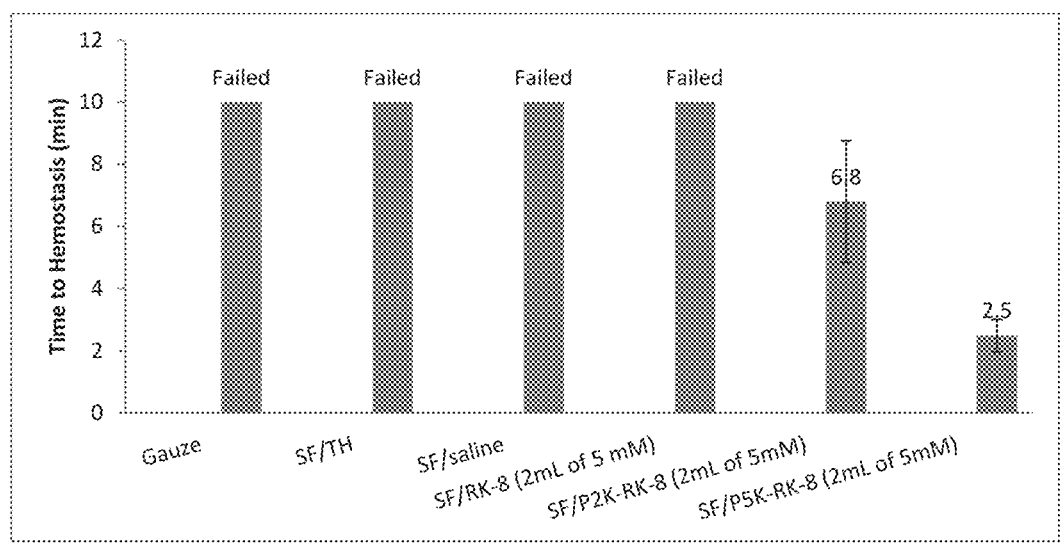
FIG. 7 shows data on time to hemostasis for several tested systems in heparinized blood.

Referring now to FIG. 7, data on time to hemostasis in minutes is presented for several tested systems and controls, using heparinized blood.

The model was Heparinized Porcine spleen biopsy punch model: 6 mm wide×3 mm deep, tamponade time: 30 sec; observation time: 30 sec; activated clotting time (ACT) was maintained above 300 seconds by infusing additional 2000 IU heparin solution if needed. 9975 IU of heparin solution was initially applied to a 39.1 Kg porcine.

As can be seen from the data presented:

Gauze (as a negative control), was used without any additional hemostatic active material) has failed as hemostat in heparinized blood;

Surgiflo™ with thrombin (designated as SF/TH) mixture has failed as hemostat in heparinized blood;

Surgiflo™ with normal saline (designated as SF/Saline) mixture has failed as hemostat in heparinized blood;

Surgiflo™ with 2 mL of 5 mM SEQ ID NO: 1 in saline solution (designated as SF/RK-8) has failed as hemostat in heparinized blood;

Surgiflo™ with 2 mL of 5 mM PEG2000-SEQ ID NO: 1 in saline solution (designated as SF/P2K-RK-8) has provided some hemostatic effect but with a time to hemostasis being too long to be practical, 6.8 min;

Surgiflo™ with 2 mL of 5 mM PEG5000-SEQ ID NO: 1 in saline solution (designated as SF/P5K-RK-8) has provided significant hemostatic efficacy.

Thus pegylated SEQ ID NO: 1, specifically PEG-5000 conjugated to SEQ ID NO: 1, showed superior hemostatic efficacy vs. thrombin, non-pegylated SEQ ID NO: 1, and other controls in heparinized blood.

EXAMPLE 8

In a bench top experiment, a synthetic porous pad was treated with pegylated SEQ ID NO: 1 in saline solution or with control solution of saline to evaluate interaction with blood. Samples were prepared by adding 100 µL of pegylated SEQ ID NO: 1 in normal saline solution (0.5 mM) or 200 µL of normal saline solution to 0.025 g Monocryl (poliglecaprone 25) pad. The impregnated Monocryl* (poliglecaprone 25) pads were then air-dried for 2 hrs following by an 1-hr vacuum drying process.

150 µL of fresh porcine blood was then added to each pad separately, and allowed it sit at room temperature for 2 minutes. The pads were then transferred to a Petri dish containing 20 mL of saline solution, observing non-coagulated blood diffusing out from the pads. A significant amount of coagulated blood was observed trapped in a pegylated SEQ ID NO: 1 treated Monocryl pad, while strong diffusion of non-coagulated blood from the control pad was also observed. Thus the pegylated SEQ ID NO: 1 was shown as promoting rapid blood coagulation.

EXAMPLE 9

In a bench top experiment, pegylated SEQ ID NO: 1 in normal saline solution, non-pegylated SEQ ID NO: 1 in normal saline solution, and control solution of normal saline were tested to evaluate interaction with blood. Samples were prepared by adding 100 µL of pegylated SEQ ID NO: 1 in normal saline solution (0.5 mM), SEQ ID NO: 1 in normal saline solution (0.5 mM), and normal saline to separate glass vials containing 100 µL of porcine blood containing sodium citrate (0.105M). Clouding of blood was instantly observed when the pegylated SEQ ID NO: 1 or SEQ ID NO: 1 solution was added to blood, while no clouding was observed in the vial with the control solution of normal saline. A complete precipitation of blood was observed after 2 hrs in vials containing pegylated SEQ ID NO: 1 or SEQ ID NO: 1, while no complete precipitation of blood was observed in the vial with the control solution of normal saline. Thus the pegylated SEQ ID NO: 1 and non-pegylated SEQ ID NO: 1 was shown as promoting rapid blood coagulation.

EXAMPLE 10

Figure 8:
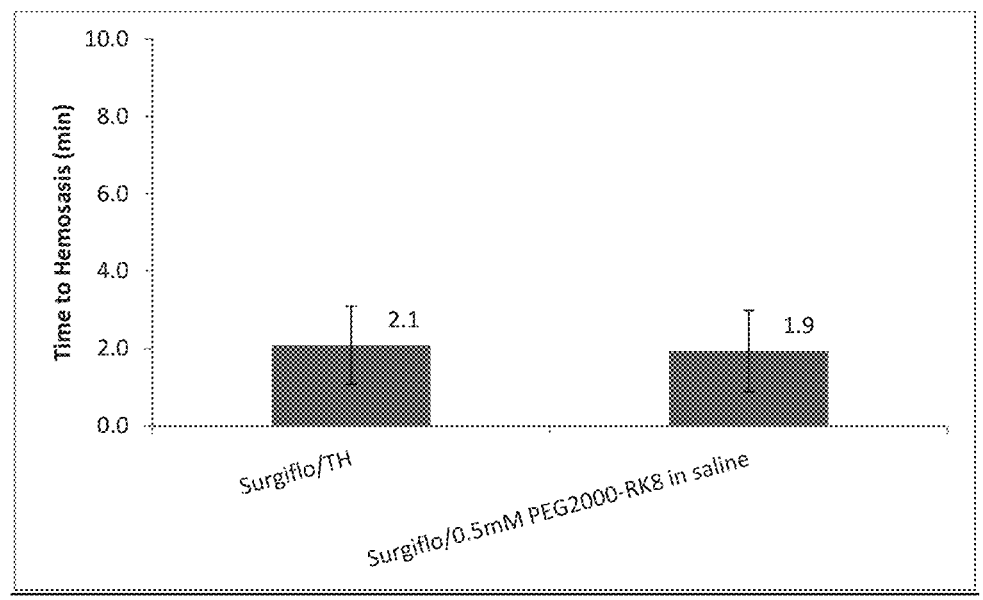
FIG. 8 shows data on time to hemostasis for two tested systems in a platelet inactivated model.

Referring now to FIG. 8, data on time to hemostasis in minutes is presented for two tested systems, all including Surgiflo™, and different types of controls or additives for improved hemostasis, including:

0.5 mM of SEQ ID NO: 1 peptide conjugated with PEG 2000 in saline (designated on the chart as Surgiflo/0.5 mM PEG2000-RK8 in saline);

Control: Surgiflo™ with human thrombin (designated as Surgiflo/TH).

The data was collected using a clopidogrel and acetylsalicylic acid treated porcine spleen biopsy punch model (6 mm wide×3 mm deep, tamponade time: 30 sec; observation time: 30 sec; the following oral dosages were applied to a 4-month-old female porcine (weight: 66.1 Kg):

2 days prior to the lab: 300 mg of Plavix and 325 mg of aspirin.

1 day prior to the lab: 75 mg of Plavix and 325 mg of aspirin.

The day for the lab: 75 mg of Plavix and 325 mg of aspirin before the surgery.

The data presented in FIG. 8 demonstrates that Surgiflo/Pegylated SEQ ID NO: 1 peptide is working as well as Surgiflo/Thrombin in a platelet inactivated model and shows a similar hemostatic efficacy. Thus not only SEQ ID NO: 1 peptide demonstrates hemostatic efficacy in the non-compromised blood, in the heparinized blood, but also in the platelet inactivated blood.

We claim:

1. A method of making a hemostatic or tissue sealing material comprising the steps of:
   (a) providing a peptide sequence selected from SEQ ID NOs.: 1-5 or their analog peptide sequence thereof, said peptide optionally conjugated to a polyethylene glycol;
   (b) providing an absorbable hemostatic scaffold wherein said hemostatic scaffold is a dry crosslinked gelatin in particle form; and
   (c) mixing said peptide and said absorbable scaffold with a liquid carrier to form a substantially homogenous hemostatic or tissue sealing material.

2. The method of claim 1 wherein said amino acid analog sequence is obtained from said sequence SEQ ID NO: 1 with at least one of the amino acids substituted with corresponding analog amino acids.

3. The method of claim 1 wherein said amino acid analog sequence is selected from the group consisting of SEQ ID NO: 2, SEQ ID NO: 3, SEQ ID NO: 4, SEQ ID NO: 5, and combinations thereof.

4. The method of claim 1 wherein said peptide is conjugated to a polyethylene glycol and the concentration of said peptide in said hemostatic material is from about 0.0025 mM to about 1.25 mM, and wherein said polyethylene glycol has a molecular weight from about 2000 to about 5000 Daltons.

5. The method of claim 1 wherein concentration of said peptide in said hemostatic material is from about 0.0025 mM to about 1.25 mM.

6. The method of claim 1 wherein said peptide is conjugated to a biocompatible polymer.

7. The method of claim 6 wherein said biocompatible polymer is a hydrophilic polymer.

8. The method of claim 7 wherein said hydrophilic polymer is selected from the group consisting of polyethylene glycol, derivative of the polyethylene glycol, polypropylene glycol, polysaccharide, modified polysaccharide, protein, modified protein, peptide, polylactide glycolide, caprolactone, trimethylene carbonate, starch, modified starch, gelatin, collagen, and combinations thereof.

9. The method of claim 6 wherein the hydrophilic polymer is polyethylene glycol having a molecular weight selected to provide for a rapid hemostasis or for a rapid tissue sealing.

10. The method of claim 9 wherein said polyethylene glycol molecule is a linear molecule, a branched molecule, a star-shaped molecule, or combinations thereof.

11. The method of claim 10 wherein said molecular weight is on average from about 1000 Daltons to about 8000 Daltons.

12. The method of claim 10 wherein said molecular weight is on average 2000 Daltons.

13. The method of claim 10 wherein said molecular weight is on average 5000 Daltons.

14. The method of claim 1 wherein step c) comprises the step of mixing the dry gelatin particles and hemostatic peptide with the liquid carrier to form a uniform paste by mixing in a confined space or using a double planetary mixer.

15. The method of claim 1 wherein the gelatin in particle form in step b) is prepared by milling dry crosslinked gelatin into particles having an average diameter of from about 40 microns to about 1200 microns.

\* \* \* \* \*

SEQUENCE LISTING

<160> NUMBER OF SEQ ID NOS: 21

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Phe Tyr Val Val Met Trp Lys
1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Arg Phe Tyr Val Val Met Trp Lys Lys
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Phe Tyr Val Val Met
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Phe Ile Arg Val Val Met Tyr Glu Gly Lys Lys
1               5                   10

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Arg Val Val Met
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 6

Arg Phe Tyr Leu Leu Met Trp Lys
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Tyr Phe Leu Leu Gln Phe Arg
1               5

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Phe Tyr Val Val Met Trp Lys Gln Val Thr Gln Ser
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Phe Leu Leu Arg Asn Pro Asn Asp Lys Tyr Glu Pro Phe
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Phe Leu Leu Arg Asn Pro Asn Asp Lys Tyr Glu Pro
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Phe Leu Leu Arg Asn Pro Asn Asp Lys Tyr Glu
1               5                   10

<210> SEQ ID NO 12

-continued

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Phe Leu Leu Arg Asn Pro Asn Asp Lys Tyr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Phe Leu Leu Arg Asn Pro Asn Asp Lys
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Phe Leu Leu Arg Asn Pro Asn Asp
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Phe Leu Leu Arg Asn Pro Asn
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Phe Leu Leu Arg Asn Pro
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17
```

```
Ser Phe Leu Leu Arg Asn
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Phe Leu Leu Arg
1               5

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Phe Leu Leu
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Val Ala Val
1

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Val Tyr Arg Trp Phe Met Val
1               5
```